(12) United States Patent
Afzali-Ardakani et al.

(10) Patent No.: US 8,764,968 B2
(45) Date of Patent: *Jul. 1, 2014

(54) DNA SEQUENCING USING MULTIPLE METAL LAYER STRUCTURE WITH ORGANIC COATINGS FORMING TRANSIENT BONDING TO DNA BASES

(75) Inventors: Ali Afzali-Ardakani, Ossining, NY (US); Stefan Harrer, Hampton (AU); Binquan Luan, Pleasantville, NY (US); Glenn J. Martyna, Croton on Hudson, NY (US); Hongbo Peng, Chappaqua, NY (US); Stephen M. Rossnagel, Pleasantville, NY (US); Gustavo A. Stolovitzky, Riverdale, NY (US); Philip S. Waggoner, Fishkill, NY (US); George F. Walker, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/607,070

(22) Filed: Sep. 7, 2012

(65) Prior Publication Data

US 2013/0001082 A1    Jan. 3, 2013

Related U.S. Application Data

(63) Continuation of application No. 13/359,750, filed on Jan. 27, 2012.

(60) Provisional application No. 61/437,101, filed on Jan. 28, 2011.

(51) Int. Cl.
*G01N 27/327* (2006.01)

(52) U.S. Cl.
USPC ............... 205/792; 204/403.01; 204/403.03; 977/957; 977/962

(58) Field of Classification Search
USPC ............ 204/403.01–403.15; 205/777.5, 778, 205/792; 600/309–367; 977/920–922, 924, 977/957–959, 962; 435/4–40.52
See application file for complete search history.

(56) References Cited

U.S. PATENT DOCUMENTS

| | | | |
|---|---|---|---|
| 4,576,829 | A | 3/1986 | Kaganowicz et al. |
| 4,692,992 | A | 9/1987 | Hsu |

(Continued)

FOREIGN PATENT DOCUMENTS

| | | |
|---|---|---|
| EP | 0261592 A1 | 9/1987 |
| EP | 1441213 | 7/2004 |

(Continued)

OTHER PUBLICATIONS

He et al. "Identification of DNA Basepairing via Tunnel-Current Decay" Nano Letters 2007 vol. 7, No. 12 p. 3854-3858.*

(Continued)

*Primary Examiner* — Susan D Leong
(74) *Attorney, Agent, or Firm* — Cantor Colburn LLP; Vazken Alexanian

(57) ABSTRACT

A technique for nanodevice is provided. A reservoir is filled with an ionic fluid. A membrane separates the reservoir, and the membrane includes electrode layers separated by insulating layers in which the electrode layers have an organic coating. A nanopore is formed through the membrane, and the organic coating on the electrode layers forms transient bonds to a base of a molecule in the nanopore. When a first voltage is applied to the electrode layers a tunneling current is generated by the base in the nanopore, and the tunneling current travels through the transient bonds formed to the base to be measured as a current signature for distinguishing the base.

5 Claims, 7 Drawing Sheets

(56) References Cited

U.S. PATENT DOCUMENTS

| | | | |
|---|---|---|---|
| 5,671,086 | A | 9/1997 | Parvin et al. |
| 6,180,490 | B1 | 1/2001 | Vassiliev et al. |
| 6,217,872 | B1 | 4/2001 | Okayama et al. |
| 6,413,792 | B1 | 7/2002 | Sauer et al. |
| 6,582,926 | B1 * | 6/2003 | Chilkoti ............... 435/7.1 |
| 6,621,191 | B1 * | 9/2003 | Nomura et al. ........... 310/309 |
| 6,627,067 | B1 | 9/2003 | Branton et al. |
| 6,727,174 | B1 | 4/2004 | Kotecki et al. |
| 6,777,260 | B1 | 8/2004 | Chen |
| 6,962,849 | B1 | 11/2005 | Kamal et al. |
| 7,282,130 | B2 | 10/2007 | Flory |
| 7,347,921 | B2 | 3/2008 | Barth et al. |
| 7,351,648 | B2 | 4/2008 | Furukawa et al. |
| 7,468,271 | B2 | 12/2008 | Golovchenko et al. |
| 7,540,717 | B2 | 6/2009 | Sheng et al. |
| 7,553,730 | B2 | 6/2009 | Barth et al. |
| 7,560,141 | B1 | 7/2009 | Kim et al. |
| 7,846,738 | B2 | 12/2010 | Golovchenko et al. |
| 2005/0019784 | A1 | 1/2005 | Su et al. |
| 2005/0026238 | A1 * | 2/2005 | Berndt ............... 435/34 |
| 2005/0101100 | A1 | 5/2005 | Kretchmer et al. |
| 2005/0110990 | A1 | 5/2005 | Koo et al. |
| 2005/0158763 | A1 | 7/2005 | Ivanisevic et al. |
| 2006/0105553 | A1 | 5/2006 | Wellhausen |
| 2006/0154399 | A1 | 7/2006 | Sauer et al. |
| 2006/0169588 | A1 | 8/2006 | Jacobson et al. |
| 2006/0180469 | A1 | 8/2006 | Han et al. |
| 2006/0246497 | A1 | 11/2006 | Huang et al. |
| 2007/0020146 | A1 | 1/2007 | Young et al. |
| 2007/0042366 | A1 | 2/2007 | Ling |
| 2007/0048745 | A1 | 3/2007 | Joyce et al. |
| 2007/0138132 | A1 | 6/2007 | Barth |
| 2007/0187694 | A1 | 8/2007 | Pfeiffer |
| 2007/0190542 | A1 | 8/2007 | Ling et al. |
| 2008/0003571 | A1 | 1/2008 | McKernan et al. |
| 2008/0032290 | A1 | 2/2008 | Young |
| 2008/0102504 | A1 | 5/2008 | Akeson et al. |
| 2008/0119366 | A1 | 5/2008 | Sauer et al. |
| 2008/0171316 | A1 | 7/2008 | Golovchenko et al. |
| 2008/0187915 | A1 * | 8/2008 | Polonsky et al. ........... 435/6 |
| 2008/0257859 | A1 | 10/2008 | Golovchenko et al. |
| 2009/0136958 | A1 | 5/2009 | Gershow et al. |
| 2009/0188794 | A1 | 7/2009 | Simon et al. |
| 2009/0221443 | A1 | 9/2009 | Heller et al. |
| 2009/0222216 | A1 | 9/2009 | Hibbs et al. |
| 2010/0025249 | A1 | 2/2010 | Polonsky et al. |
| 2010/0084276 | A1 | 4/2010 | Lindsay |
| 2010/0327255 | A1 | 12/2010 | Peng et al. |
| 2010/0327847 | A1 | 12/2010 | Leiber et al. |
| 2010/0331194 | A1 | 12/2010 | Turner et al. |
| 2011/0052813 | A1 | 3/2011 | Ho et al. |
| 2011/0085759 | A1 * | 4/2011 | Lee et al. ............... 385/12 |
| 2011/0220574 | A1 | 9/2011 | Bakajin et al. |
| 2011/0236984 | A1 | 9/2011 | Sun et al. |
| 2011/0279125 | A1 | 11/2011 | Bedell et al. |
| 2012/0146162 | A1 | 6/2012 | Cho et al. |
| 2012/0193235 | A1 * | 8/2012 | Afzali-Ardakani et al. .. 204/601 |
| 2012/0193236 | A1 * | 8/2012 | Peng et al. ............... 204/603 |
| 2012/0193237 | A1 * | 8/2012 | Afzali-Ardakani et al. .. 204/627 |
| 2013/0037410 | A1 | 2/2013 | Xu et al. |
| 2013/0203050 | A1 | 8/2013 | Huber et al. |

FOREIGN PATENT DOCUMENTS

| | | |
|---|---|---|
| EP | 1486775 A | 12/2004 |
| WO | WO0181908 A | 11/2001 |
| WO | WO2006122317 | 11/2006 |
| WO | WO2007084163 A | 7/2007 |
| WO | WO2008051308 A2 | 5/2008 |
| WO | WO2008132643 A1 | 11/2008 |
| WO | WO2009020682 A2 | 2/2009 |
| WO | WO2009032756 A2 | 3/2009 |

OTHER PUBLICATIONS

U.S. Appl. No. 12/820,543, filed Jun. 22, 2012; First Named Inventor: Ali Afzali-Ardakani.

U.S. Appl. No. 13/248,176; Title: Selective Placement of Carbon Nanotubes via Coulombic Attraction of Oppositely Charged Carbon Nonotubes and Self-Assembled Monolayers, filed Sep. 29, 2011; First Named Inventor: Ali Afzali-Ardakani.

Hongbo Peng, et al., pending U.S. Appl. No. No. 13/359,729, entitled "Electron Beam Sculpting of Tunneling Junction for Nanopore DNA Sequencing," filed with the U.S. Patent and Trademark Office on Jan. 27, 2012.

Hongbo Peng, et al., pend U.S. Appl. No. 13/359,743, entitled "DNA Motion Control Based on Nanopore with Organic Coating Forming Transient Bonding to DNA," filed with the U.S. Patent and Trademark Office on Jan. 27, 2012.

Hongbo Peng, et al., pending U.S. Appl. No. 13/359,750, entitled "DNA Sequencing Using Multiple Metal Layer Structure with Organic Coatings Transient Bonding to DNA Bases," filed with the U.S. Patent and Trademark Office on Jan. 27, 2012.

Hong Peng, et al., pending U.S. Appl. No. 13/359,766, entitled "DNA Sequencing Using Multiple Metal Layer Structure with Different Organic Coatings Forming Different Transient Bondings to DNA," filed with the U.S. Patent and Trademark Office on Jan. 27, 2012.

A Bergvall et al., "Graphene nanogap for gate-tunable quantum-coherent single-molecule electronics," Phys. Rev. B, vol. 84, No. 15, 2011, 155451, 7 pages.

A. J. Storm et al., "Fabrication of solid-state nanopores with single-nanometre precision," Nature Materials, vol. 2, Aug. 2003, pp. 537-540.

R. Akeson M., Branton D., Kasianowicz J., Brandin E. and Deamer D.W., "Microsecond Timescale Discrimination Among Polysytidylic Acid, Polyadenylic Acid, and Polyuridylic Acid as Homopolymers or as Segments Within Single RNA Molecules," Biophys. J., 77 3227-33 (1999), 7 pages.

Amit Meller et al., "Rapid nanopore discrimination between single polynucleotide molecules," PNAS, Feb. 1, 2000, vol. 97, No. 3, pp. 1079-1084.

Branton, Daniel, et al., "The potential and challenges of nanopore sequencing" NIH Public Access—Author Manuscript, Nat Biotechnol. available in PMC May 18, 2009, pp. 1-17.

Gracheva, Maria E. et al., "Simulation of the electric response of DNA translocation through a semiconductor nanopore—capacitor", Institute of Physics Publishing, Nanotechnology, vol. 17 (2006), pp. 622-633.

Heng, Jiunn B. et al., "Sizing DNA Using a Nanometer-Diameter Pore", Biophysical Journal, vol. 87, Oct. 2004, pp. 2905-2911.

Kasianowicz, John J., et al., "Characterization of individual polynucleotide molecules using a membrane channel", Proc. Natl. Acad. Sci. USA, vol. 93, Nov. 1996, pp. 13770-13773.

Lagerqvist, Johan et al., "Fast DNA Sequencing via Transverse Electronic Transport", Nano Lett., vol. 6, No. 4, revised Manuscript, pp. 779-782.

Soni, Gautam V. et al., "Progress toward Ultrafast DNA Sequencing Using Solid-State Nanopores", Clinical Chemistry, vol. 53, No. 11, (2007), pp. 1-6.

Douville, et al., "DNA Linearization Through Confinement in Nanofluidic Channels, Anal Bioanal Chem.", Aug. 2008; vol. 391; No. 7; pp. 2395-2409; Abstract; p. 2402, col. 2; para 5; p. 2406; col. 2; para 2; p. 2407; Fig. 5b.

B. Luan et al., "Tribological Effects on DNA Translocation in a Nanochannel Coated with a Self-Assembled Monolayer," J. Phys. Chem. B, vol. 114, 2010, pp. 17172-17176; Nov. 12, 2010.

Bae, S. et al., "Roll-to-Roll Production of 30-inch Graphene Films for Transparent Electrodes," Nature Nanotechnology, Published online: Jun. 20, 2010, 5 pages.

D. Branton et al., "The Potential and Challenges of DNA Sequencing," Nat. Biotech., vol. 26 (10), pp. 1146-1153 (2008).

I. Braslavsky, B. Hebert, E. Kartalov, S. R. Quake, "Sequence Information Can Be Obtained from Single DNA Molecules," Proc. Natl. Acad. Sci. USA, vol. 100, pp. 3960-3964 (2003).

(56) References Cited

OTHER PUBLICATIONS

F. S. Collins, M. Morgan, A. Patrinos, "The Human Genome Project—Lessons From Large-scale Biology," Science, vol. 300, pp. 286-290 (2003).

D. W. Hess, "Plasma-assisted oxidation, anodization, and nitridation of silicon," IBM J. Res. Develop. vol. 43. No. 1/2, Jan./Mar. 1999, pp. 127-145.

M. Fedurco, A. Romieu, S. Williams, I. Lawrence, G. Turcatti, "BTA, a Novel Reagent for DNA Attachment on Glass and Efficient Generation of Solid-phase Amplified DNA Colonies," Nucleic Acids Res. vol. 34, pp. e22 (2006).

A. K. Geim and K. S. Novoselov, "The Rise of Graphene," Nature Materials 6, 183 (2007), 9 pages.

Gracheva M E, Xiong A, Aksimentiev A, Schulten K, Timp G and Leburton J P, "Simulation of the Electric Response of DNA Translocation Through a Semiconductor Nanopore-capacitor," Nanotechnology, Published Jan. 6, 2006, Online: stacks.iop.org/Nano/17/622; 12 pages.

S. Harrer et al. "Electrochemical Characterization of Thin Film Electrodes Towards Developing a DNA-Transistor," Langmuir, vol. 26 (24), pp. 19191-19198 (2010).

S. Harrer et al., "Electrochemical Protection of Thin Film Electrodes in Solid State Nanopore," Nanotechnology, vol. 22, 2011, 275304, 6 pages.

T. D. Harris et al., "Single-molecule DNA Sequencing of a Viral Genome," Science, vol. 320, pp. 106-109 (2008).

J. Hass, W.A. De Heer and E.H. Conrad, "The Growth and Morphology of Epitaxial Multilayer Graphene," Journal of Physics: Condensed Matter 20, 323202 (2008), 28 pages.

Heng J B, Ho C, Kim T, Timp R, Aksimentiev A, Grinkova Y V, Sligar S, Schulten K and Timp G, "Sizing DNA Using a Nanometer-diameter Pore," Biophys Journal vol. 87, 2905-2911 (Oct. 2004); 7 pages.

H.W.C. Postma, "Rapid Sequencing of Individual DNA Molecules in Graphene Nanogaps," Nano Letters, vol. 10, No. 2, Jan. 4, 2010, pp. 420-425.

International Search Report—PCT; Notification of Transmittal of the International Search Report and the Written Opinion of the International Searching Authority, or the Declaration; Apr. 5, 2011; International application No. PCT/ US1123872; 8 pages.

J. Prasongkit et al., "Transverse conductance of DNA necleotides in a graphene nanogap from first principles," arXiv:1012.1669v2 [physics.ins-det], [v1] Dec. 8, 2010, [v2] Jan. 14, 2011, Nano Lett., vol. 11, No. 5, 2011, pp. 1941-1945.

J. J. Kasianowicz, E. Brandin, D. Branton, D. W. Deamer, "Characterization of Individual Polynucleotide Molecules Using a Membrane Channel," Proc. Natl. Acad. Sci. USA., vol. 93, pp. 13770-13773 (1996).

K.S. Kim, Y. Zhao, H. Jang, S. Y. Lee, J. M. Kim, K. S. Kim, J. H. Ahn, P. Kim, J. Y. Choi, B. H. Hong, "Large-Scale Pattern Growth of Graphene Films for Stretchable Transparent Electrodes," Nature 457, 706-710 (2009).

Lagerqvist J, Zwolak M and Di Ventra M, "Fast DNA Sequencing Via Transverse Electronic Transport," Nano Lett. 6 779-782 (2006).

B. Luan, H. Peng, S. Polonsky, S. Rossnagel, G. Stolovitzky, and G. Martyna, "Base-by-base Ratcheting of Single-stranded DNA Through a Solid-state Nanopore," Phys. Rev. Lett., vol. 104 (23) pp. 238103-1-238103-4 (2010).

B. Luan, A. Aksimentiev, "Control and Reversal of the Electrophoretic Force on DNA in a Charged Nanopore," J. Phys. Condens. Matter, vol. 22, pp. 454123 (2010).

B. Luan et al., "Tribological Effects on DNA Translocation in a Nanochannel Coated with a Self-Assembled Monolayer," J. Phys. Chem. B, vol. 114, 2010, pp. 17172-17176.

M. J. Kim et al., "Rapid Fabrication of Uniformly Sized Nanopores and Nanopore Arrays for Parallel DNA Analysis," Adv. Mater. 2006, 18, pp. 3149-3153.

M. Margulies et al., "Genome Sequencing in Mircrofabricated High-density Pico-litre Reactors," Nature, vol. 437, pp. 376-380 (2005).

Meller A., Nivon L., Brandin E., Golovchenko J. and Branton D., "Rapid Nanopore Discrimination Between Signle Polynucleotide Molecules," Proc. Natl Acad. Sci. USA 97 1079-84 (2000).

United States Patent and Trademark Office, Non-Final Office Action for U.S. Appl. No. 12/704,665, pp. 1-15.

Novoselov K S et al, "Electric Field Effect in Atomically Thin Carbon Films" Science, American Association for the Advancement of Science, US, Washington, DC, vol. 306, No. 5696, Oct. 11, 2004, pp. 666-669, XP009086357, ISSN: 0036-8075, the whole document.

Fernando Patolsky, Gengfeng Zheng, Oliver Hayden, Melike Lakadamyali, Xiaowei Zhuang, and Charles M. Lieber, "Electrical detection of single viruses," Departments of Chemistry and Chemical Biology and Physics and Division of Engineering and Applied Sciences, Harvard University, Cambridge, MA 02138, Contributed by Charles M. Lieber, Aug. 20, 2004, pp. 1-6.

Polonsky et al., "Nanopore in metal-dielectric sandwich for DNA position control," Applied Physics Letters 91, 153103 (2007).

F. Sanger, S. Nicklen, A. R. Coulson, "DNA sequencing with chain termination inhibitors," Proc. Natl. Acad. Sci USA., vol. 74 (12), pp. 5463-5467 (1977).

Schedin F et al: "Detection of Individual Gas Molecules Absorbed on Graphene" Nature Materials Nature Publishing Group, UK, vol. 6, No. 9, Sep. 2007, pp. 652-655, XP002506772, ISSN: 1476-1122, the whole document.

J. Shedure et al., "Accurate Multiplex Polony Sequencing of an Evolved Bacterial Genome," Science, vol. 309, pp. 1728-1732 (2005).

G. Sigalov, et al., "Detection of DNA Sequences Using an Alternating Electric Field in a Nanopore Capacitor," Nano Letters 2008, vol. 8, No. 1; pp. 56-63.

H. Stranneheim, et al., "Stepping Stones in DNA Sequencing," Biotechnical Journal (2012) 7 (9) pp. 1063-1073.

* cited by examiner

DNA SEQUENCING USING MULTIPLE METAL LAYER STRUCTURE WITH ORGANIC COATINGS FORMING TRANSIENT BONDING TO DNA BASES

CROSS-REFERENCE TO RELATED APPLICATIONS AND PRIORITY CLAIM

This application is a continuation of U.S. Non-Provisional application Ser. No. 13/359,750, entitled "DNA SEQUENCING USING MULTIPLE METAL LAYER STRUCTURE WITH ORGANIC COATINGS FORMING TRANSIENT BONDING TO DNA BASES", filed Jan. 27, 2012, which is based on and claims priority to U.S. Provisional Patent Application 61/437,101, entitled "DNA SEQUENCING USING MULTIPLE METAL LAYER STRUCTURE WITH ORGANIC COATINGS FORMING TRANSIENT BONDING TO DNA BASES", filed Jan. 28, 2011, both of which are incorporated herein by reference in their entirety.

BACKGROUND

Exemplary embodiments relate to nanodevices, and more specifically to sequencing using a multiple layer structure in a nanodevice.

Recently, there has been growing interest in applying nanopores as sensors for rapid analysis of biomolecules such as Deoxyribonucleic acid (DNA), Ribonucleic acid (RNA), protein, etc. Special emphasis has been given to applications of nanopores for DNA sequencing, as this technology holds the promise to reduce the cost of sequencing below $1000/human genome. Two issues in these applications of nanopores are the control of the translocation of DNA through the nanopore and differentiating DNA bases.

Nanopore sequencing is a method for determining the order in which nucleotides occur on a strand of DNA. A nanopore is simply a small hole on the order of several nanometers in internal diameter. The theory behind nanopore sequencing has to do with what occurs when the nanopore is immersed in a conducting fluid and an electric potential (voltage) is applied across it: under these conditions a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be put around the nanopore so that DNA bases can be differentiated while the DNA passes through the nanopore.

DNA could be driven through the nanopore by using various methods. For example, an electric field might attract the DNA towards the nanopore, and it might eventually pass through it. Also, enzymes attached to the nanopore might guide DNA towards the nanopore. The scale of the nanopore means that the DNA may be forced through the hole as a long string, one base at a time, rather like thread through the eye of a needle.

BRIEF SUMMARY

According to an exemplary embodiment, a method for controlling a molecule in a nanodevice is provided. The method includes filling a reservoir with ionic fluid, and configuring a membrane to separate the reservoir. The membrane includes electrode layers separated by insulating layers in which the electrode layers have an organic coating. The method includes forming a nanopore through the membrane, where the organic coating on the electrode layers forms transient bonds to a base of the molecule in the nanopore. When a first voltage is applied to the electrode layers a tunneling current is generated by the base in the nanopore, and the tunneling current travels through the transient bonds formed to the base to be measured as a current signature for distinguishing the base.

According to an exemplary embodiment, a method for controlling a molecule in a nanodevice is provided. The method includes forming a nanochannel in a substrate, and the nanochannel connects two reservoirs. The nanochannel and the two reservoirs are filled with ionic fluid. The method includes configuring a pair of electrodes having a nanometer size gap there between, where the pair of electrodes is positioned along the nanochannel and in the substrate. The method includes configuring an organic coating on an exposed surface of the pair of electrodes at an inner surface of the nanochannel, where the organic coating forms transient bonds between the pair of electrodes and a base of a molecule in the nanochannel. When a first voltage is applied to the pair of electrodes a tunneling current is generated by the base in the nanochannel, and the tunneling current travels through the transient bonds formed to the base to be measured as a current signature for distinguishing the base.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

DETAILED DESCRIPTION

Exemplary embodiments are based on an organic-coated nanopore through a stack of repetitive insulating/conducting/insulating/conducting/insulating/ . . . layers. Exemplary embodiments are configured to leverage the transient bonding between the organic coating and the DNA bases to control the motion of the DNA, and then utilize the tunneling current through the DNA base for differentiating the DNA base while the DNA base is transiently bonded to the organic coating. This is called a transient bond because an external electric field can by applied to move the DNA molecule and thus break the transient bond to the DNA base.

Exemplary embodiments may use a nanopore through a stack of repetitive insulating/conducting/insulating/conducting/insulating/ ... layers where all conductive surfaces (of the conducting/electrode layers) at the inner-surface of the nanopore are coated with an organic coating. This organic coating can transiently bond to individual DNA bases and thus the DNA can be temporarily trapped inside the nanopore when enough of these transient bonds are present. The negative-charged DNA can be controllably driven through the nanopore by an external electrical field along the nanopore when the external electrical fields alternate between being above and below the threshold for breaking all transient bonds. All conducting layers are electrically addressed to a voltage source, and the tunneling current between adjacent conducting layers is measured while individual DNA bases are temporaly fixed/bonded to these conducting layers. Since DNA bases are temporarily fixed during the measurements, the tunneling current will have enough resolution to differentiate DNA bases. Note that multiple conducting layers (resulting in multiple bonding locations) provide the appropriate trapping energy to trap the DNA and provide redundant data of tunneling current for error check. DNA can also be driven back and forth through the nanopore many times by switching the polarity of the external electrical fields, for repeated measurements and double checking previous measurements.

Figure 1:
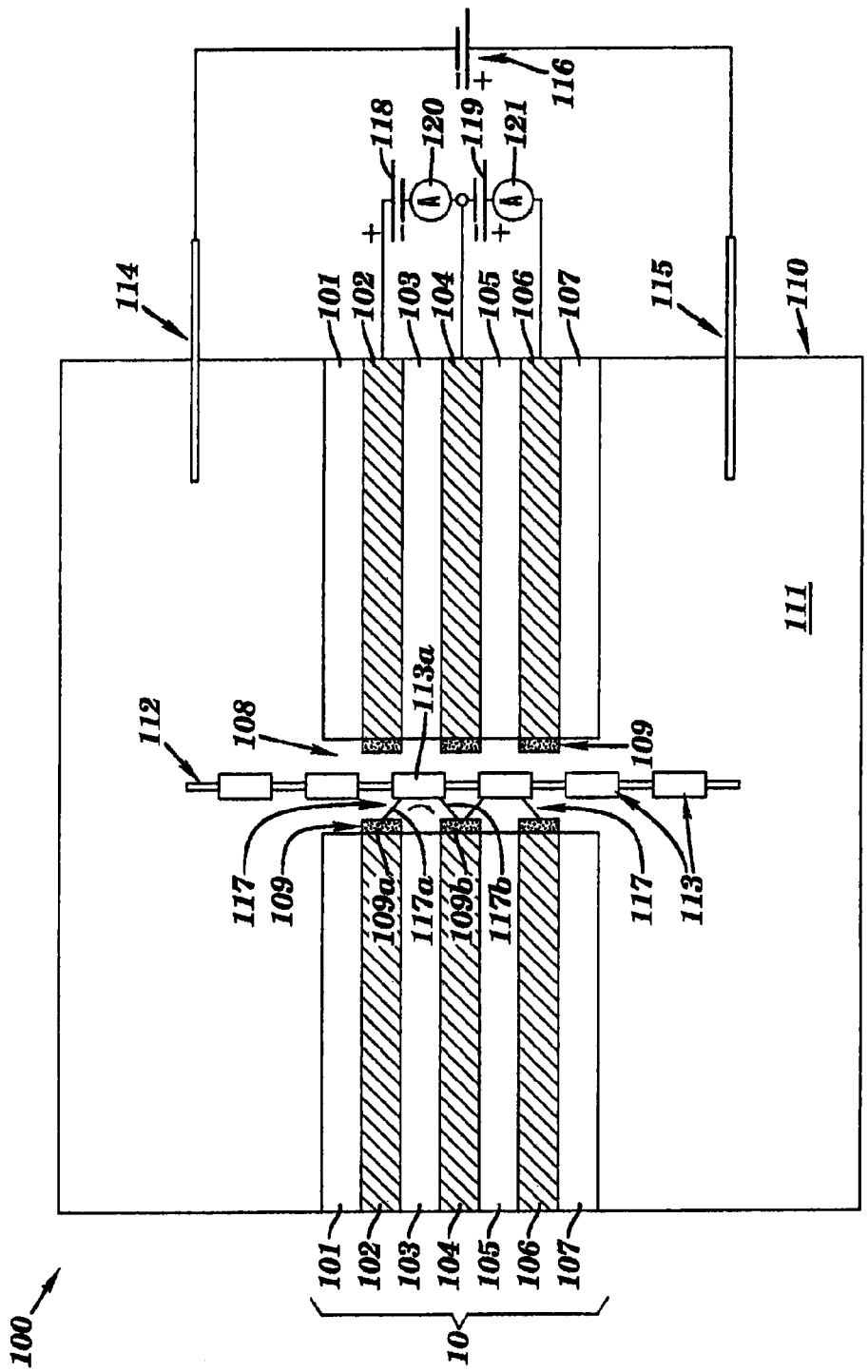
FIG. 1 illustrates a cross-sectional schematic of a nanodevice in accordance with an exemplary embodiment.

Now turning to the figures, FIG. 1 illustrates a cross-sectional schematic of a nanodevice 100 having an organic-coated nanopore through a stack of repetitive insulating/conducting/insulating/conducting/insulating/ ... layers for DNA motion control and base sensing according to an exemplary embodiment. The nanodevice 100 is configured to measure tunneling current through a single DNA base according to an exemplary embodiment.

In FIG. 1, a membrane 10 partitions a reservoir 110 into two parts. A nanometer size (hole) nanopore 108 is made through the membrane 10. The membrane 10 includes electrically insulating layers 101, 103, 105, and 107 and electrically conducting layers 102, 104, and 106, which are all films. The insulating layers 101 and 107 are electrical passivation layers, and the insulating layers 103 and 105 are insulating inter-layers between conducting layers 102, 104, and 106. Only three conducting layers 102, 104, and 106 are shown in the FIG. 1, but exemplary embodiments are not limited to three conducting layers. It is contemplated that two or more conducting layers may be utilized. The conducting layers 102, 104, and 106 are electrodes and may be referred to as electrodes or electrode layers herein.

An organic coating 109 is made on the surface of conducting layers 102, 104, and 106, and the organic coating 109 can be any organic coating that forms a transient bond 117, such as hydrogen bond, with individual DNA bases 113 of DNA molecule 112. The organic coating 109 consists of bifunctional (i.e., first functionality and second functionality) small molecules which at one end form covalent bonds with electrode layers 102, 104, and 106, and this is the first functionality; at the other end (of the bifunctional small molecules of the organic coating 109) which is exposed in the nanopore 108, the organic coating 109 consists of a second functionality which can form strong hydrogen bonds with the DNA molecule 112 and/or can protonate nucleotides to form acid base interactions.

The first functionality of the organic coating 109 forms the covalent bond that attaches to the electrode layers 102, 104, and 106. In a first case example of the first functionality, the electrode layers 102, 104, and 106 (i.e., conducting layers) may be made of metals such as gold, palladium, platinum, etc. In this first case example, the covalent bonding functionality (i.e., first functionality) of the bifunctional molecules for the organic coating 109 which bonds to electrode layers 102, 104, and 106 can be chosen from, but is not limited to, thiols, isocyanides, and/or diazonium salts. In a second case example, the electrode layers 102, 104, and 106 may be made of titanium nitrides or indium tin oxide. In this second case example, the covalent bonding functionality (i.e., first functionality) of the bifunctional molecules for the organic coating 109 which bonds to the electrode layers 102, 104, and 106 can be chosen from, but is not limited to, phosphonic acid, hydroxamic acid, and/or resorcinol functionality. The small bifunctional molecules (in the first and second case examples) are designed to be electrically conductive such that any charge formation due to interaction with DNA molecule 112 can easily be transferred to the electrode layers 102, 104, and 106, and therefore a pi-conjugated moiety (e.g., benzene, diphenyl, etc.) are sandwiched between two functionalities (the first and second functionality).

The second functionality of the organic coating 109 can be chosen from groups which can form a strong hydrogen bond with DNA, such as the DNA molecule 112. Examples of such a group (for the second functionality of the organic coating 109) include but are not limited to alcohols, carboxylic acids, carboxamides, sulfonamides, and/or sulfonic acids. Examples of another such group which can be used to form interactions (strong bonds) with the DNA molecule 112 are individual self-assembled nucleotides. For example, individual self-assembled nucleotides include, but are not limited to, adenine monophosphonic acid, guanine monophosphonic acid etc., which can be self-assembled on titanium nitride electrodes (electrode layers 102, 104, 106) or mercapto thymine or mercapto cytosine self-assembles on metal electrodes (electrode layers 102, 104, 106) such as gold and/or platinum.

The organic coating 109 can be made of the first and second functionalities, and applied to the electrode layers 102, 104, and 106. The discussion for the organic coating 109 along with electrode layers 102, 104, and 106 applies to organic coating 209 and electrode layers 202, 204, and 206 in FIG. 2 and applies to organic coating 307 and 308 and electrode pairs 305 and 306 in FIG. 3.

Referring to FIG. 1, the minimum number of electrode layers 102, 104, and 106 is determined by the need (as desired by a user) for trapping DNA molecules 112 inside the nanopore 108 against thermal agitation via the transient bonds 117. The reservoir 110 and the nanopore 108 are then filled with ionic solvent 111. The ionic solvent 111 (including ionic solvents 211 and 309) can be any salt dissolved in any solvent (water or organic solvent) with any pH depending on the application. One example of the solvent 111 includes a KCl (potassium chloride) solution in water with a pH range from 6-9 for DNA translocation.

DNA molecules 112 (in which bases are illustrated as 113) are loaded into the nanopore 108 by an electrical voltage bias of voltage source 116, applied across the nanopore 108 via two electrochemical electrodes 114 and 115, which were dipped in the solvent 111 of the two parts of the reservoir 110. The voltage source 116 causes the external electric field for moving the DNA molecule 112.

With enough electrode layers 102, 104, and 106 (e.g., two or more), thus enough transient bonds 117, the DNA molecule 112 can be trapped inside the nanopore 108 against thermal motion. With predefined voltage applied by voltage source 116, these transient bonds 117 can be broken, and the DNA molecule 112 can be driven through the nanopore 108 via the electrical field produced by the voltage source 116. If the voltage of the voltage source 116 is pulsed, the DNA molecule 112 can be controlled to experience a bonded phase (by the transient bonds 117 holding the DNA molecule 112 in place) and a moving phase (by the voltage of voltage source 116 breaking the transient bonds 117). At the bonded phase, voltages of voltage sources 118 and 119 can be applied between neighboring electrode layers 102 and 104 and electrode layers 104 and 106 respectively. Tunneling current (A) 120 and tunneling current (A) 121 can be measured with ammeters (ampere meters) which are used for measuring electrical current. Since a DNA base 113 is fixed, these current signatures of the tunneling currents 120 and 121 can be used to identify individual DNA bases 113 from different DNA bases 113 on the DNA molecule 112. The moving phase will advance the DNA molecule 112 (through the nanopore 108) for identifying other DNA bases 113. The DNA molecule 112 can also be driven back and forth through the nanopore 108 many times by switching the polarity of the external voltage bias of the voltage source 116, for repeated measurements of the same DNA bases 113.

The organic coating 109 should be at least made on the surface of electrode layers 102, 104 and 106 that are inside of the nanopore 108. Additionally, in some embodiments, the organic coating 109 can also be made on the surface of the insulating layers 101, 103, 105, 107 that are inside of the nanopore 108, to enhance the trapping (via additional transient bonds not shown) of DNA molecules 112 inside the nanopore 108.

For example, when the DNA molecule 112 is driven into the nanopore 108 by voltage of the voltage source 116, a DNA base 113a (which is designated as one of the DNA bases 113) forms a transient bond 117 via the organic coating 109 (which will be designated as organic coating 109a and 109b for explanation purposes) with the electrode layer 102 and the electrode layer 104. The organic coating 109 applied on the ends of the electrode layers 102 and 104 forms a chemical bond with DNA base 113a which is called the transient bond 117. For explanation purposes to ease understanding, the transient bonds 117a and 117b connecting the DNA base 113a to electrode layers 102 and 104 may be viewed as wires connecting the DNA base 113a to the electrode layers 102 and 104. When the voltage source 118 is turned on, current flows through electrode layer 102, then through organic coating 109a, through the transient bond 117a, into the DNA base 113a (which causes tunneling current), out through the transient bond 117b, into the organic coating 109b, into electrode layer 104, and into the ammeter for measuring the tunneling current 120 of the DNA base 113a. The measured tunneling current 120 is a unique current signature of the DNA base 113a. This process can be applied simultaneously for all the DNA bases 113 having transient bonds 117 to the electrode layers 102, 104, and 106 although one example was provided above for DNA base 113a.

Note that, the tunneling current 120 between electrode layers 102 and 104 (via DNA base 113) does not require any electrical wiring between the electrode layers 102 and 104, as electrons simply move from one electrode layer 102 (via DNA base 113) to the other electrode layer 104 in a quantum mechanical way, as understood by one skilled in the art. There will be a baseline tunneling current (of a particular amount) when DNA base 113a is away (with distance much longer than the wavelength of an electron) from the two electrode layers 102 and 104. When DNA base 113a is close (within the distance of the wavelength of an electron) to the two electrode layers 102 and 104, the tunneling path of the electron will be rerouted to tunnel from one electrode (e.g., electrode layer 102) to the DNA base 113a and then to the other electrode (e.g., electrode layer 104). In this way, the tunneling electrode layers 102 and 104 will create a signature (such as an increasing of tunneling current, typically in the order of tens of pA (picoamperes) added onto the baseline tunneling current trace (i.e., the particular amount of tunneling current measured when the DNA base 113 is greater than the distance of one wavelength of an electron). The tunneling current (generated) across DNA bases 113 is dependent upon the electronic and chemical structure of the DNA bases 113, and thus different DNA bases 113 will generate a different tunneling current signature. The organic coating 109 and the transient bonds 117 help to fix the orientation of the DNA base 113 and fix the relative distance of the DNA base 113 to the electrodes (e.g., electrode layers 102 and 104) for improving the resolution of the tunneling current signatures (e.g., the tunneling current 120 and 121 measured by the ammeter). If the organic coating 109 and/or transient bonds 117 are electrically conductive, they will help to shrink the tunneling gap size and also enhance (increase) the tunneling current signatures. If the difference between the tunneling current signatures of different DNA bases is small or stochastic, repeating measurements on the same DNA base can be done; a histogram of the amplitudes of the tunneling current signatures can be fit and the statistical data will provide enough resolution to differentiate DNA bases.

Although the example explains how the two electrode layers 102 and 104 are used to measure the tunneling current 120 for DNA base 113a in the nanopore 108, any two of the electrode layers 102, 104, and 106 can be utilized to measure any of the DNA bases 113 within their vicinity. For example, when the DNA base 113a is driven further through the nanopore 108, the tunneling current 121 for DNA base 113a can be measured with electrode layers 104 and 106 using voltage applied by the voltage source 119. The tunneling current 120 measured for DNA base 113a can be compared (by software application 505) against the tunneling current 121 measured for the DNA base 113a (after the DNA base 113a has advanced through the nanopore 108 to form transient bonds 117 with electrodes layers 104 and 106). Also, with multiple layers of electrode layers and insulating layers in the membrane 10 and with multiple voltage sources and ammeters, the tunneling current for different DNA bases 113 can be simultaneously measured in the nanopore 108.

Figure 2:
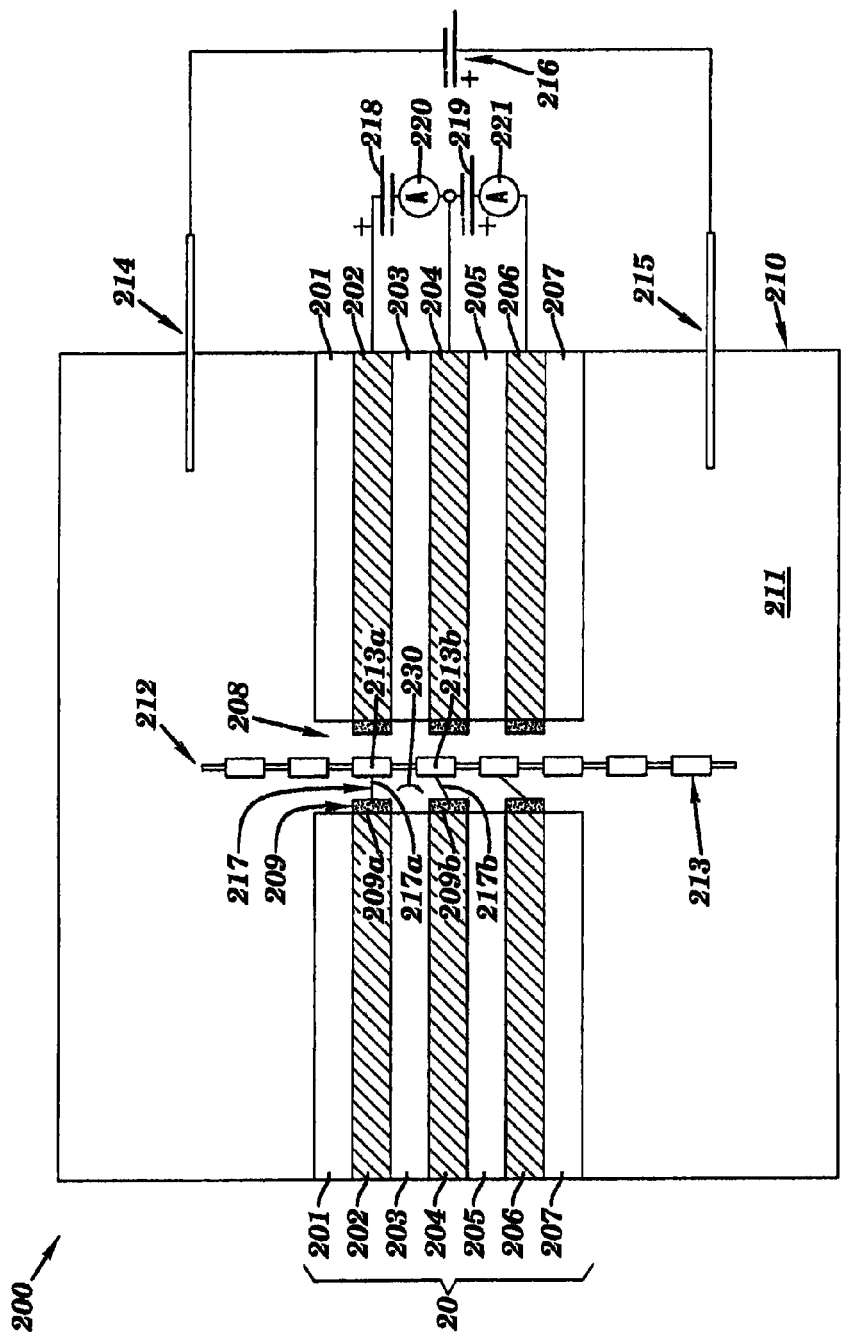
FIG. 2 illustrates a cross-sectional schematic of a nanodevice in accordance with an exemplary embodiment.

Now turning to FIG. 2, this diagram illustrates a cross-sectional schematic of a nanodevice 200 having an organic-coated nanopore through a stack of repetitive insulating/conducting/insulating/conducting/insulating/ . . . layers for DNA motion control and base sensing, for the case that tunneling current is measured through a sequence of several DNA bases according to an exemplary embodiment.

In FIG. 2, a membrane 20 partitions a reservoir 210 into two parts. A nanometer size (hole) nanopore 208 is made through the membrane 20, and the reservoir is filed with an ionic solvent 211 (fluid). The membrane 20 includes electrically insulating layers 201, 203, 205, and 207 and electrically conducting layers 202, 204, and 206, which are all films. The insulating layers 201 and 207 are electrical passivation layers, and the insulating layers 203 and 205 are insulating interlayers between conductive layers. Three electrically conducting layers 202, 204, and 206 are shown in the FIG. 2, but exemplary embodiments are not limited to three conducting layers. It is contemplated that two or more conducting layers may be utilized. The conducting layers 202, 204, and 206 are electrodes and may be referred to as electrodes or electrode layers herein. An organic coating 209 is made on the surface of conducting layers 202, 204, and 206, and the organic coating 209 can be any organic coating that can form transient bond 217 to DNA bases 213 (as discussed above for organic coating 109).

FIG. 2 is almost identical to FIG. 1, except that the transient bonds 217 from adjacent conducting layers are linked to different DNA bases 213 instead of a single DNA base. Thus the tunneling current (signature) 220 and the tunneling current 221 will each be associated with two or more DNA bases 213 (instead of a single DNA base as in FIG. 1). This provides a faster DNA sequencing speed but requires more resolution on the tunneling signals (such as tunneling current signature for tunneling current 220) to resolve $4^n$ types of tunneling signals (where n is the number of DNA bases 213 along the tunneling path, and where 4 is the total number of different DNA bases 213).

Figure 6:
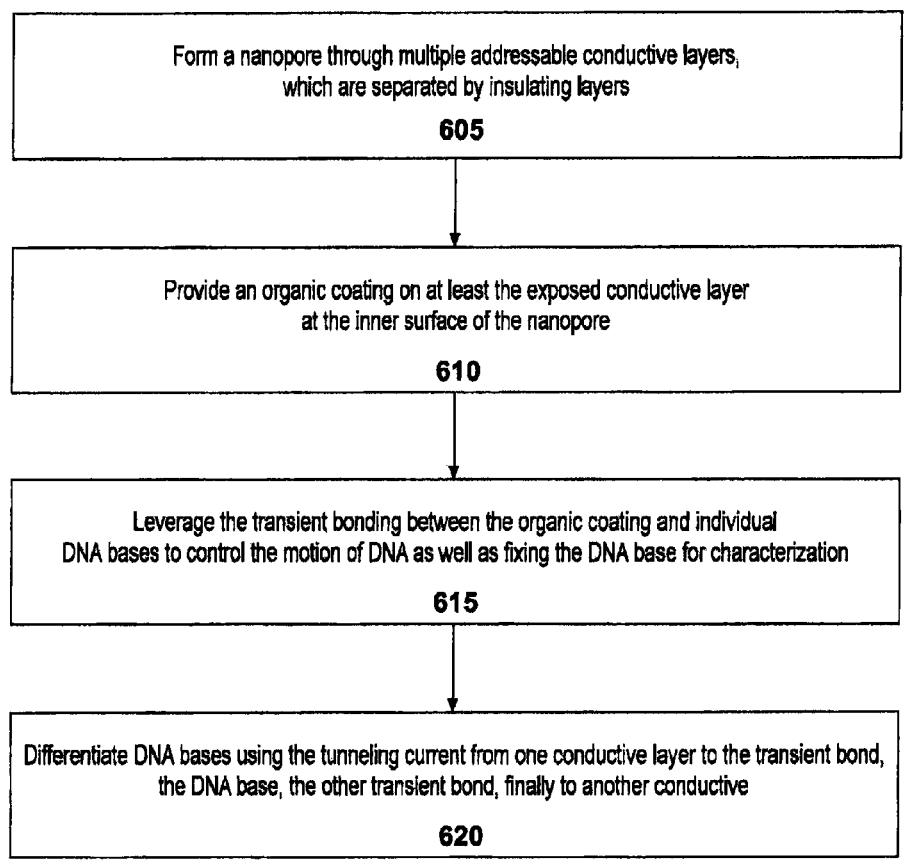
FIG. 6 is a method for controlling a molecule in a nanodevice in accordance with an exemplary embodiment.

An example tunneling path 230 will be discussed, for explanation purposes. The voltage applied by the voltage source 216 produces an external electric field to drive the DNA molecule 212 into the nanopore 208. When the voltage source 218 is turned on, current flows through electrode layer 202, through the organic coating 209a, through the transient bond 217a, into the DNA base 213a, through (the backbone of) the DNA molecule 112 (which is the line connecting DNA bases 213a and 213b), into the DNA base 213b, out through the transient bond 217b, out through the organic coating 209b, into the electrode layer 204, and into an ammeter to measure tunneling current 220. In this example, when the ammeter measures the tunneling current 220, it actually measures the tunneling current through the tunneling path 230 which is a combination of (tunneling currents generated by) the DNA base 213a and the DNA base 213b. As discussed above, the tunneling current 220 (signal) through the tunneling path 230 combined of the DNA base 213a and the DNA base 213b has to be analyzed in order to indentify/resolve individual (tunneling currents corresponding to) DNA bases 213a and 213b. FIG. 6 illustrates a computer 500 having a software application 505 configured to analyze the tunneling current 220 and thus determine the combination of the DNA base 213a and the DNA base 213b. There are 4 types of DNA bases (A, T, C and G) and a total of 16 types of combinations of the DNA base 213a and the DNA base 213b (213a and 213b could be one of such combinations: AA, AT, AC, AG, TA, TT, TC, TG, CA, CT, CC, CG, GA, GT, GC, GG). Different combinations of the DNA base 213a and the DNA base 213b will generate different tunneling current 220. If the difference between the tunneling current of different combinations of bases is small or stochastic, repeating measurements on the same combination of DNA bases can be done, a histogram of the amplitudes of the tunneling current signatures can be fit, and the statistical data will provide enough resolution to identify the exact combination of DNA bases. If DNA molecule 212 advances (by the voltage applied by voltage source 216) just one DNA base 213 after measuring the tunneling current 220 of the combination of DNA base 213a and the base DNA 213b, the new combination of DNA bases under measurement will have a difference of only one DNA base 213 from the previous measured combination. This will generate redundant/extra data for error checking by the software application 505.

Figure 3:
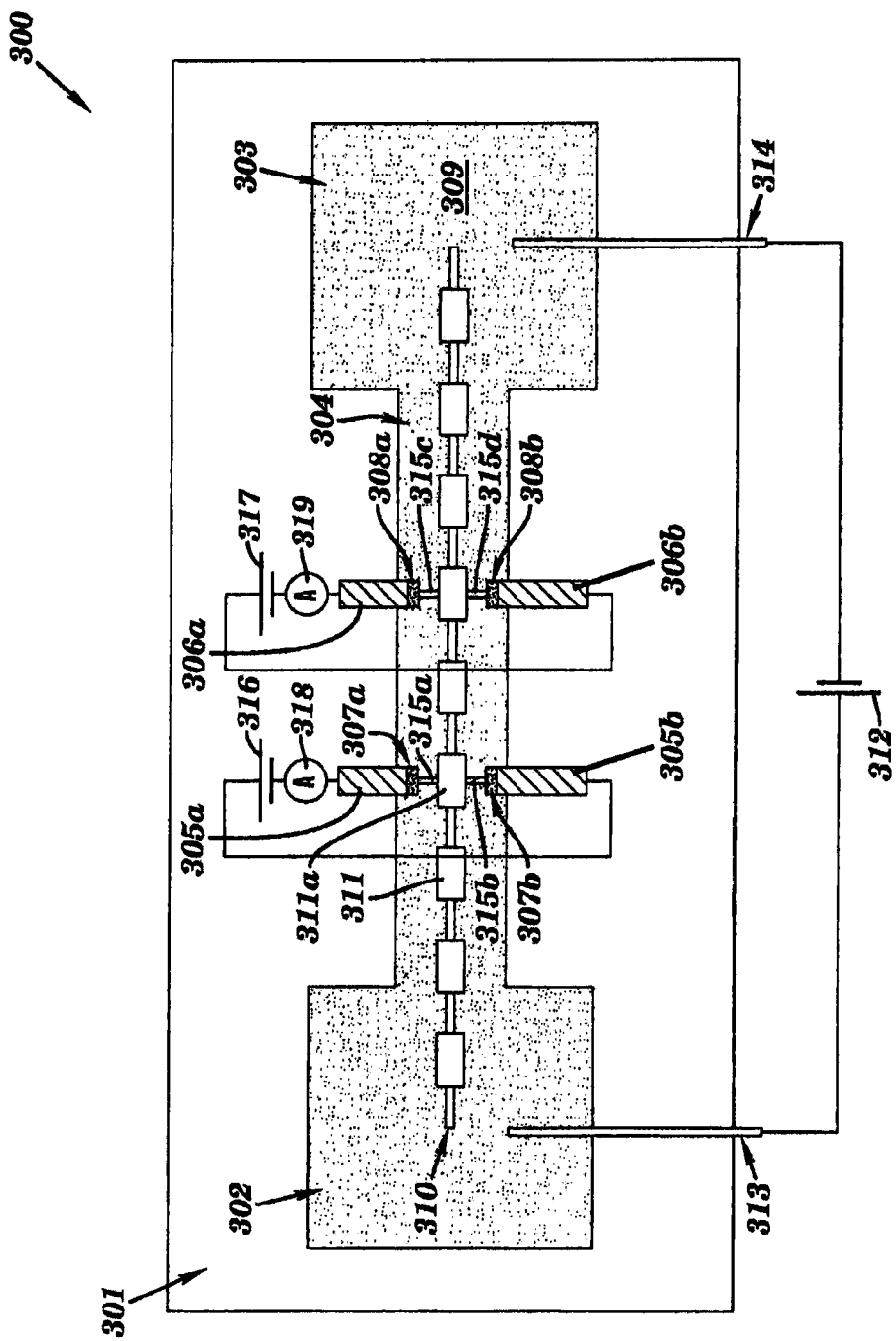
FIG. 3 illustrates a cross-sectional schematic of a nanodevice in accordance with an exemplary embodiment.

Referring to FIG. 3, this diagram illustrates a cross-sectional schematic of a nanodevice 300 having an organic-coated nanochannel with multiple tunneling electrodes for DNA motion control and base sensing according to an exemplary embodiment.

FIG. 3 illustrates a "lateral nanochannel" version of the discussions for FIGS. 1 and 2. FIG. 3 is a top cross-sectional view of the nanodevice 300. A substrate 301 may be made of any insulating and/or semiconductor solid material. Two reservoirs 302 and 303 are etched into the substrate 301, and a lateral nanochannel 304 connects them. Reservoir 302, reservoir 303, and nanochannel 304 are then filled with ionic solvent 309. Electrodes 305a and 305b are a pair of electrodes with a nanometer size gap between them, and the end of each electrode 305a and 305b is integrated within nanochannel 304 while the other end is in the substrate 301. Electrodes 306a and 306b are another pair of electrodes with a nanometer size gap between them, and the end of each electrode 306a and 306b is integrated within nanochannel 304 while the other end is in the substrate 301. Although only two pairs of electrodes (such as pair of electrodes 305a and 305b and pair of electrodes 306a and 306b) are shown in FIG. 3, it is contemplated that electrodes of one or more pairs (e.g., 6, 7, or 10 pairs of electrodes) may be utilized as discussed herein.

Organic coating 307a and 307b are respectively made on the exposed surface of electrodes 305a and 305b, and organic coating 308a and 308b are respectively made on the exposed surface of electrodes 306a and 306b. The organic coating 307 and 308 can be any organic coating that forms a transient bond 315, such as a hydrogen bond, with individual DNA bases 311 of the DNA molecule 310. The minimum number of pairs of electrodes is determined by the need (of the user) for trapping DNA molecule 310 inside the nanochannel 304 against thermal agitation via these transient bonds 315. DNA molecule 310 can be loaded into the nanochannel 304 by an electrical voltage bias of voltage source 312 (producing an external electric field) applied across the nanochannel 304 via two electrochemical electrodes 313 and 314, which were dipped in the ionic solvent 309 of the two reservoirs 302 and 303.

With enough pairs of electrodes (e.g., pair of electrodes 305a and 305b and/or pair of electrodes 306a and 306b), thus enough transient bonds 315, the DNA molecule 310 can be trapped inside the nanochannel 304 against thermal motion. With a predefined voltage applied by voltage source 312, these transient bonds 315 can be broken, and the DNA molecule 310 can be driven through the nanochannel 304 via the electrical field. If voltage of the voltage source 312 is pulsed, the DNA molecule 310 will experience a (transient) bonded phase and a moving phase. During the bonded phase, voltages sources 316 and 317 can be applied on electrode pairs 305 and 306 respectively. Tunneling currents 318 and 319 can be measured with an ammeter respectively corresponding to each tunneling current 318 and 319. Since the DNA base 311 is in a fixed bonded position by the transient bond 315, these tunneling current (signatures) 318 and 319 can be used to singly identify individual DNA bases 311 with the software application 505 of the computer 500. The moving phase will advance the DNA molecule 310 for identifying other DNA bases 311. The DNA molecule 310 can also be driven back and forth through the nanochannel 304 many times by switching the polarity of the external voltage bias of the voltage source 312, for repeated measurements.

An example of measuring the tunneling current 318 is provided below for the left circuit but also applies to the right circuit measuring tunneling current 319. When voltage of the voltage source 316 is turned on during the bonded phase, current flows through electrode 305b, through organic coating 307b, through the transient bond 315b, into DNA base 311a (which produces the tunneling current 318), out through the transient bond 315a, out through organic coating 307a, and through electrode 305a to measure the tunneling current 318 by the ammeter. In exemplary embodiments, numerous circuits (e.g., 2, 5, and/or 10) can simultaneously measure the tunneling current for numerous DNA bases of a DNA molecule, although only two circuits are shown respectively with electrode pairs 305 and 306.

The pair of electrodes 305a and 305b (similarly pair of electrodes 306a and 306b) are two separate electrodes on opposite sides of the nanochannel 304 connected by a wire at the ends not in the nanochannel 304. The ends of electrodes 305a and 305b (similarly electrodes 306a and 306b) in the nanochannel 304 which have organic coating 307a and 307b (similarly organic coatings 308a and 308b) do not touch and are not connected by a wire. Instead, the transient bonds 315a and 315b (similarly transient bonds 315c and 315d) operatively connect/couple the electrodes 305a and 305b together through the DNA base 311a via the organic coating 307a and 307b.

Figure 4:
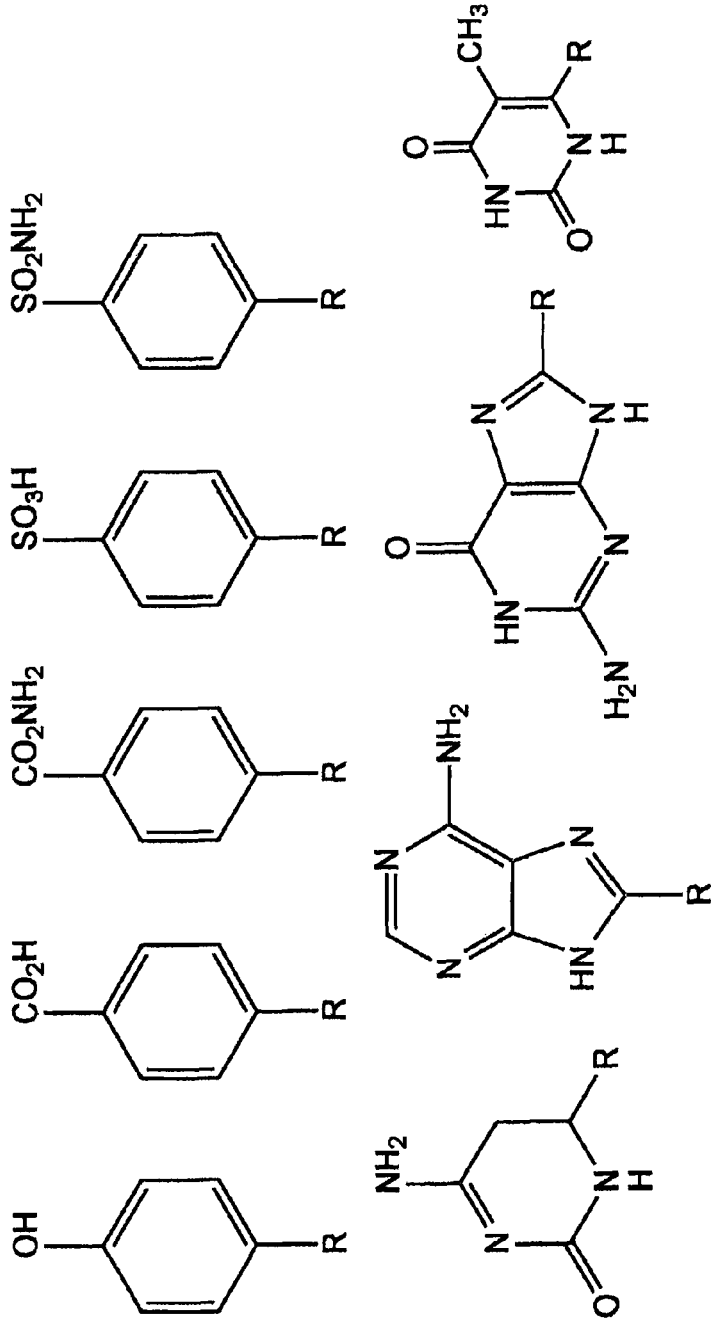
FIG. 4 illustrates example molecules of an organic coating according to an exemplary embodiment.

FIG. 4 illustrates examples of molecules/compounds that may be used for the organic coating 109 in FIG. 1, organic coating 209 in FIG. 2, and organic coatings 307 and 308 in FIG. 3, according to an exemplary embodiment. Note that the organic coatings 109, 209, 307, and 308 may be the same in one implementation.

As an example, organic coatings 109, 209, 307, and 308 can all be chosen from the compounds depicted in FIG. 4. Depending on the nature of the electrode layers, a different anchoring functionality (i.e., first functionality) can be used. For example, if the contacts (i.e., electrodes/electrode layers) are made of metals like gold, palladium or platinum, the anchoring functionality (R in FIG. 4) is chosen from thiol (—SH) or isonitrile (—NC) functionalities as would be understood by one skilled in the art according to the teaching of the disclosure. On the other hand, if the electrodes are made from titanium nitride or conductive oxides like zinc oxide, then the anchoring functionality can be chosen from phosphonic acid (—PO3H2) or hydroxamic acid (—CONHOH) as would be understood by one skilled in the art according to the teachings of the disclosure. As an example, assume that the electrodes 102, 104 and 106 are fabricated from (to be coated with) organic coating 109, reactants are selected from FIG. 4 to form electrode layers (coated) with organic titanium nitride. Then the nanodevice is immersed in a dilute (0.1 to 10 mmolar) solution of 4-carboxyphenylphosphonic acid in alcohol (methanol, ethanol or isopropyl alcohol) at room temperature for 0.5 hour to 24 hours. The nanodevice 100 is then removed from the coating solution and immersed in the pure solvent for rinsing of any non-coated material. In this process, the phosphonic acid group forms a strong bond with the titanium nitride surface (which are the coated electrode layers 102, 104, 106) and exposes the carboxylic acid group (on the coated electrode layers 102, 104, 106) inside the nanopore 108. The carboxylic acid group will form the bond with the DNA molecule in this example.

As understood by one skilled in the art, other molecules depicted in FIG. 4 can analogously be used in the same manner, but the solvent may change depending on the solubility of the compound/molecule. Other solvents which can be useful for coating these materials are water, dimethylformamide, and/or a mixture of water and alcohols. In each case, the anchoring group (R in FIG. 4) forms the covalent bond with the nitride or oxide surface (of the electrode/electrode layer) and exposes the other functionality (i.e., the second functionality that bonds to the DNA molecule in the nanopore/nanochannel).

FIG. 6 illustrates a method 600 of DNA sequencing using multiple metal and insulating layers to form transient bonds according to exemplary embodiments. Reference can be made to FIGS. 1 and 2.

At block 605, a nanopore (e.g., nanopore 108, 208) is formed through multiple addressable conducting layers (e.g., electrode layers 102, 104, 106 and electrode layers 202, 204, 206), which are separated by insulating layers (e.g., insulating layers 103, 105 and insulating layers 203, 205).

An organic coating (e.g., organic coating 109, 209) is provided on at least the exposed conducting layer at the inner surface of the nanopore at block 610. In one implementation, the organic coating can also coat insulating layers.

At block 615, the transient bonding is leveraged between the organic coating and individual DNA bases (e.g., DNA bases 113, 213) to control the motion of DNA (e.g., DNA molecule 112, 212) as well as to fix (hold) the DNA base in place for characterization (i.e., measuring the tunneling current 120, 121, 220, 221). A first voltage (e.g., applied by voltage source 118, 119, 218, 219) causes the DNA bases to generate the tunneling current.

The DNA bases are differentiated (via the computer 500) using the tunneling current (e.g., tunneling current 120 measured by an ammeter) from one conducting layer (e.g., electrode layer 102) to the transient bond (e.g., transient bond 117a), to the DNA base (e.g., DNA base 113a), to the other transient bond (e.g., transient bond 117b), and finally to another conducting layer (e.g., electrode layer 104) at block 620. Also, DNA bases are differentiated (via the computer 500) using the tunneling current (e.g., tunneling current 220 measured by an ammeter) from one conducting layer (e.g., electrode layer 202) to the transient bond (e.g., transient bond 217a), to one or more DNA bases (e.g., to the DNA base 213a and to another DNA base 213b), to the other transient bond (e.g., transient bond 217b), and finally to another conducting layer (e.g., electrode layer 204).

Further, with reference to FIG. 1, two electrode layers (e.g., electrode layers 102 and 104) hold the DNA base (e.g., DNA base 113a) in place within the nanopore against thermal motion via their respective transient bonds (e.g., transient bond 117a, 117b). Also, with reference to FIG. 2, two electrode layers (e.g., electrode layers 202 and 204) hold the DNA bases (e.g., DNA bases 213a and 213b) in place within the nanopore against thermal motion via their respective transient bonds (e.g., transient 217a, 217b).

When a second voltage is applied (e.g., by voltage source 116, 216) to move the molecule (e.g., DNA molecule 112, 212) through the nanopore such that other base (e.g., such as a DNA base 113 next in line above DNA base 113a in nanopore 108 or a DNA base 213 above DNA base 213a in nanopore 208) is in a vicinity of the electrode layers (e.g., electrode layers 102 and 104, electrode layers 202 and 204). The organic coating on the electrode layers forms the transient bonds with the other base (i.e., next in line). Accordingly, when the first voltage is applied to the electrode layers another tunneling current (just like tunneling current 120, 220) is generated by the other base (DNA base 113 next in line above DNA base 113a or a DNA base 213 above DNA base 213a), and the other tunneling current is to be measured by an ammeter as another current signature for distinguishing the other base. The computer 600 is operatively connected to the nanodevices 100, 200, and 300 to distinguish the current signatures for the respective DNA bases 113, 213, 311 even when multiple tunneling currents from multiple DNA bases are combined to make up the measured current signature as discussed herein.

For example, when the multiple DNA bases 213 (e.g., a first DNA base, second DNA base, etc) are fixed by the transient bonds 217 via the organic coating 209, tunneling current is generated by the first DNA base 213 and another tunneling current is generated by the second DNA base 213 in response to the first voltage (e.g., voltage source 218). As such, the current signature (of the combined tunneling current 220) includes the tunneling current and the other tunneling current. The current signature for the combined tunneling current 220 is resolved (by the software application 605) to distinguish the first DNA base 213 from the second DNA base 213. Note that, although the explanation above mentions the tunneling current and the other tunneling for ease of understanding, there is (only) one tunneling current 220 generated by both the DNA bases 213a and 213b. That is, these DNA bases 213a and 313b generate a combined tunneling current 220 because there is only one tunneling current that tunnels through the two (or more) DNA bases 213a and 213b at the same time. This will create a tunneling current signal (i.e., combined tunneling current 220) based on the two areas (as one unit). As such, the tunneling current 220 can be through (and/or result from) two or more DNA bases 213 at the same time.

Figure 7:
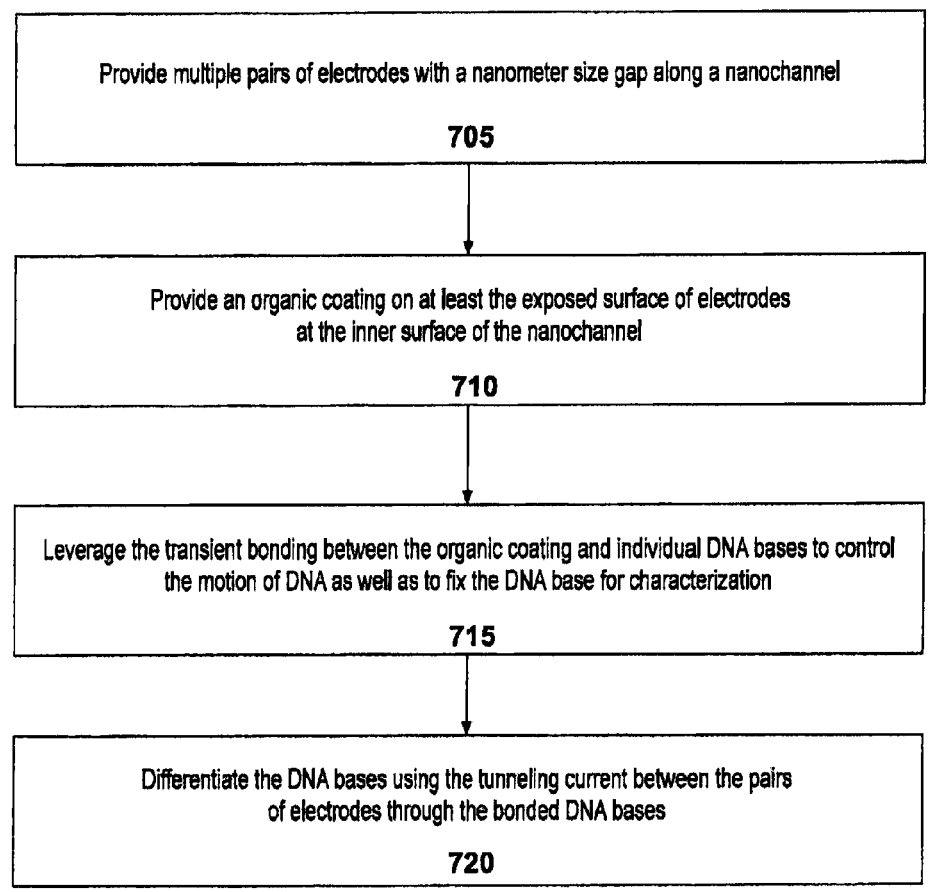
FIG. 7 is a method for controlling a molecule in a nanodevice in accordance with an exemplary embodiment.

FIG. 7 illustrates a method 700 of DNA sequencing using multiple metal and insulating layers to form transient bonds according to exemplary embodiments. Reference can be made to FIG. 3.

Multiple pairs (or a single pair) of electrodes (e.g., pair of electrodes 305 and/or 306) with a nanometer size gap there between are provided along a nanochannel (e.g., nanochannel 304) connecting two reservoirs (e.g., reservoirs 302 and 303) at block 805. The nanochannel and the two reservoirs are filled with ionic fluid 309.

An organic coating (e.g., organic coatings 307 and/or 308) is provided on at least the exposed surface of electrodes (e.g., pair of electrodes 305 and/or 306) at the inner surface of the nanochannel at block 710. The organic coating can also coat other parts of the nanochannel. At block 715, the transient bonding (e.g., transient bonds 315) is leveraged between the organic coating and individual DNA bases (e.g., DNA bases 311) to control the motion of a DNA molecule (e.g., DNA molecule 310) as well as to fix/bind the DNA base in place for tunneling current measurement and characterization by the computer 500.

When a first voltage (from voltage sources 316, 317) is applied to the pair of electrodes (e.g., pair of electrodes 305a and 305b and/or 306a and 306b), DNA bases are differentiated using the tunneling current (e.g., tunneling current 318, 319 as respective current signatures) between the pairs of electrodes through the bonded DNA bases (e.g., DNA base 311a) at block 720.

Further, a second voltage (from voltage source 312) is applied to move the DNA molecule (from left to right in this example) through the nanochannel such that another base is in a vicinity of the pair of electrodes (pair of electrodes 305 and 306). As such, the organic coating on the pair of electrodes forms the transient bonds with the other base, e.g., the DNA base 311 to the left of DNA base 311a would be moved into the vicinity of the pair of electrodes 305a and 305b such that the transient bonds 315a and 315b are now bonded to the recently moved DNA base 311. The same occurs for the DNA base 311 now being moved into the vicinity of the pair of electrodes 306a and 306b, such that transient bonds 315c and 315d fix the DNA base 311 now moved into the vicinity of the pair of electrodes 306a and 306b. As such, when the first voltage is applied (e.g., by voltage sources 316 and 317) to the respective pair of electrodes another tunneling current is generated by the other base (e.g., the DNA base recently moved into the vicinity), and the other tunneling current is measured as another current signature (just as the tunneling currents 318 and 319 are measured) for distinguishing the other base. In FIG. 3, the tunneling currents 318 and 319 can be concurrently measured for two separate DNA bases 311 within the vicinity (e.g., fixed by the transient bonds 315a and 315b and transient bonds 315c and 315d) of the pairs of electrodes 305 and 306, respectively.

Figure 5:
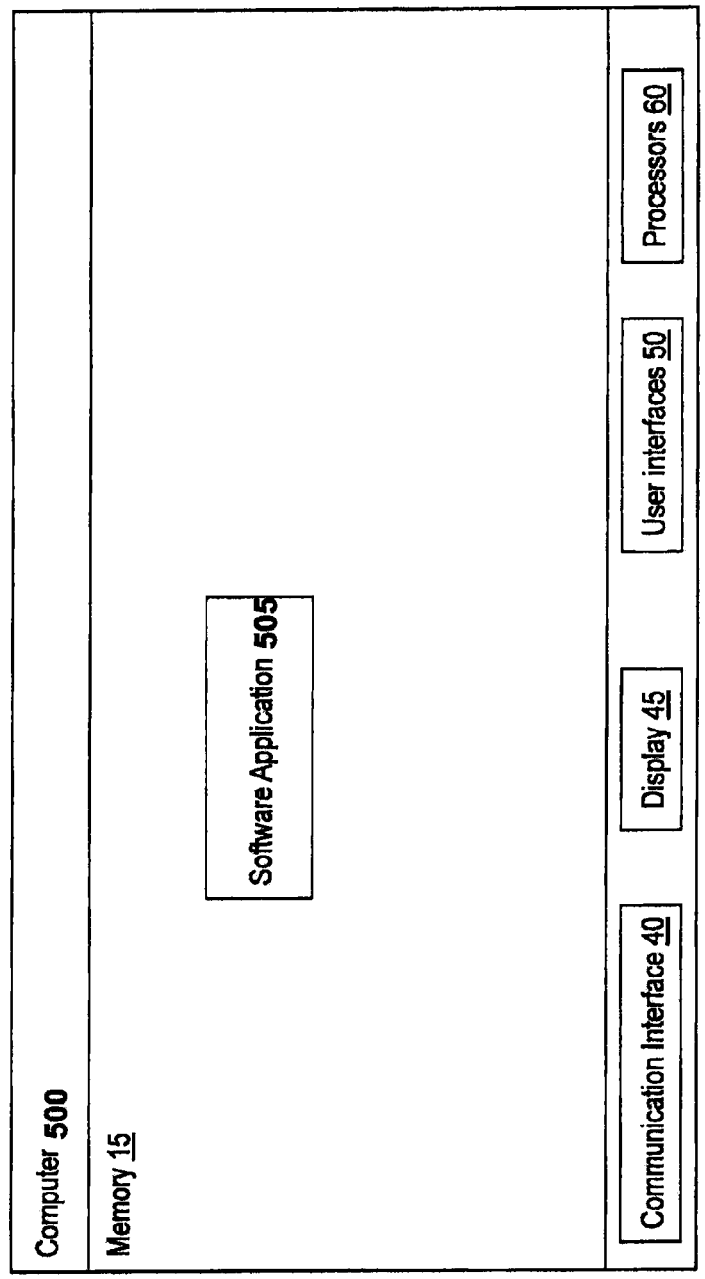
FIG. 5 illustrates a computer utilized for characterizing the tunneling currents/current signatures of bases of a molecule in accordance with an exemplary embodiment.

Now turning to FIG. 5, FIG. 5 illustrates a block diagram of a computer 500 having various software and hardware elements for implementing exemplary embodiments.

The diagram depicts the computer 500 which may be any type of computing device and/or test equipment. The computer 500 may include and/or be coupled to memory 15, a communication interface 40, display 45, user interfaces 50, processors 60, and software 605. The communication interface 40 comprises hardware and software for communicating over a network and connecting (via cables, plugs, wires, electrodes, etc.) to the nanodevices 100, 200, and 300 discussed herein. Also, the communication interface 40 comprises hardware and software for communicating with, reading, and controlling voltage sources, ammeters, tunneling currents, etc., as discussed herein. The user interfaces 50 may include, e.g., a track ball, mouse, pointing device, keyboard, touch screen, etc, for interacting with the computer 500, such as inputting information, making selections, independently controlling different voltages sources, displaying, viewing and recording tunneling current signatures for each base, etc. In one implementation, the computer 500 may include the voltage sources and ammeters discussed herein.

The computer 500 includes memory 15 which may be a computer readable storage medium. One or more applications such as the software application 505 (e.g., a software tool) may reside on or be coupled to the memory 15, and the software application 505 comprises logic and software components to operate and function in accordance with exemplary embodiments in the form of computer executable instructions. The software application 505 may include a graphical user interface (GUI) which the user can view and interact with according to exemplary embodiments.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method for controlling a molecule in a nanodevice, comprising:
   filling a reservoir with ionic fluid;
   configuring a membrane to separate the reservoir, the membrane comprises electrode layers separated by insulating layers in which the electrode layers have an organic coating;
   forming a nanopore through the membrane, the organic coating on the electrode layers forms transient bonds to a base of the molecule in the nanopore;
   wherein, when a first voltage is applied to the electrode layers, a tunneling current is generated by the base in the nanopore, such that the tunneling current travels through the transient bonds formed to the base to be measured as a current signature for distinguishing the base; and
   breaking the transient bonds of the organic coating by applying an electric field above a threshold for breaking the transient bonds;
   wherein to attach to the electrode layers, the organic coating includes a selection from thiols, isocyanides, diazonium salts, phosphonic acid, hydroxamic acid, and resorcinol based on a type of material of the electrode layers; and
   wherein to form the transient bonds with the base, the organic coating includes a selection from alcohols, carboxylic acids, carboxamides, sulfonamides, and sulfonic acids.

2. The method of claim 1, wherein two electrode layers of the electrode layers are configured to form the transient bonds with the base via the organic coating; and
   wherein the two electrode layers hold the base in place within the nanopore against thermal motion.

3. The method of claim 1, wherein a second voltage is applied to move the molecule through the nanopore such that another base can be loaded to a vicinity of the electrode layers;
   wherein the organic coating on the electrode layers forms the transient bonds with the another base; and
   wherein when the first voltage is applied to the electrode layers another tunneling current is generated by the another base, the another tunneling current to be measured as another current signature for distinguishing the another base.

4. The method of claim 1, wherein when the base and another base are fixed by the transient bonds via the organic coating, the tunneling current is generated by the base and another tunneling current is generated by the another base in response to the first voltage;
   wherein the current signature comprises the tunneling current and the another tunneling current; and
   wherein the current signature is resolved to distinguish the base from the another base.

5. The method of claim 1, wherein the organic coating on the electrode layers forms the transient bonds to a plurality of bases of the molecule in the nanopore; and
   wherein, when the first voltage is applied to the electrode layers, the tunneling current concurrently travels through the plurality of bases, such that the current signature is based on the plurality of bases in the nanopore.

* * * * *